United States Patent
Durham et al.

(10) Patent No.: US 9,864,844 B2
(45) Date of Patent: Jan. 9, 2018

(54) WEARABLE DEVICE NORMALIZATION OF FITNESS EQUIPMENT SETTINGS AND CHARACTERISTICS

(71) Applicant: Intel Corporation, Santa Clara, CA (US)

(72) Inventors: Lenitra M. Durham, Beaverton, OR (US); Giuseppe Raffa, Portland, OR (US); Glen J. Anderson, Beaverton, OR (US); Deepak S. Vembar, Portland, OR (US); Jamie Sherman, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/751,191

(22) Filed: Jun. 26, 2015

(65) Prior Publication Data

US 2016/0375307 A1    Dec. 29, 2016

(51) Int. Cl.
*A63B 24/00* (2006.01)
*G06F 19/00* (2011.01)
*A61B 5/11* (2006.01)

(52) U.S. Cl.
CPC .......... *G06F 19/3481* (2013.01); *A61B 5/112* (2013.01)

(58) Field of Classification Search
CPC ............ A63B 24/0087; A63B 24/0062; A63B 2024/0096
See application file for complete search history.

(56) References Cited

U.S. PATENT DOCUMENTS

| 5,218,865 A | 6/1999 | Djorup |
| 6,450,922 B1 | 9/2002 | Henderson et al. |
| 9,216,320 B2 * | 12/2015 | Ishii ................ A63B 24/0087 |
| 2008/0090703 A1 | 4/2008 | Rosenberg |
| 2013/0165195 A1 * | 6/2013 | Watterson .......... A63B 71/0616 463/6 |
| 2013/0178334 A1 | 7/2013 | Brammer |
| 2013/0274587 A1 | 10/2013 | Coza et al. |

(Continued)

FOREIGN PATENT DOCUMENTS

WO    2014022438 A1    2/2014

OTHER PUBLICATIONS

International Search Report and Written Opinion for International Patent Application No. PCT/US2016/033033, dated Jul. 29, 2016, 99 pages.

(Continued)

*Primary Examiner* — Loan H Thanh
*Assistant Examiner* — Megan Anderson
(74) *Attorney, Agent, or Firm* — Jordan IP Law, LLC (57) ABSTRACT

Systems and methods may provide for obtaining first wearable sensor data associated with a first fitness session and first fitness equipment and obtaining second wearable sensor data associated with a second fitness session and second fitness equipment. Additionally, an effort normalization may be conducted between one or more settings of the second fitness equipment and one or more settings of the first fitness equipment based on the first wearable sensor data and the second wearable sensor data. In one example, a user prompt is generated during the second fitness session via a user interface of one or more of the second fitness equipment or a wearable device based on the normalization.

6 Claims, 4 Drawing Sheets

(56) References Cited

U.S. PATENT DOCUMENTS

| | | | |
|---|---|---|---|
| 2014/0100678 A1 | 4/2014 | Chapa et al. | |
| 2014/0135173 A1* | 5/2014 | Watterson | A63B 24/0087 |
| | | | 482/8 |
| 2014/0142459 A1 | 5/2014 | Jayalth et al. | |
| 2014/0280137 A1* | 9/2014 | Anderson | G06F 17/30309 |
| | | | 707/737 |
| 2014/0379106 A1* | 12/2014 | Weast | G06F 1/163 |
| | | | 700/91 |
| 2015/0111698 A1* | 4/2015 | Abbondanza | A63B 24/0087 |
| | | | 482/4 |
| 2015/0238817 A1 | 8/2015 | Watterson et al. | |
| 2016/0059076 A1* | 3/2016 | Ishii | A63B 24/0087 |
| | | | 434/247 |
| 2016/0129310 A1 | 5/2016 | Ahmed et al. | |
| 2016/0213980 A1 | 7/2016 | Chen | |
| 2016/0256745 A1* | 9/2016 | Brammer | A63B 71/0622 |

OTHER PUBLICATIONS

Office Action for U.S. Appl. No. 14/866,100, dated Apr. 19, 2017, 21 pages.

Germano, Beth, Cambridge Company Creates Wheel That Turns Any Bicycle Into a Hybrid Electric, boston.cbslocal.com/2013/12/06/cambridge-company-creates-wheel-that-turns-any-bicycle-into-a-hybrid-electric/, Dec. 6, 2013, CBS Boston, 4 pages.

Wang, Yu-Hsiang, et al., A Microcantilever-based Gas Flow Sensor for Flow Rate and Direction Detection, CTIP of MEMS & MOEMS, Apr. 9-11, 2008, English Abstract, 3 pages.

Notice of Allowance for U.S. Appl. No. 14/866,100, dated Aug. 24, 2017, 9 pages.

Notice of Allowability for U.S. Appl. No. 14/866,100, dated Sep. 25, 2017, 6 pages.

* cited by examiner

WEARABLE DEVICE NORMALIZATION OF FITNESS EQUIPMENT SETTINGS AND CHARACTERISTICS

TECHNICAL FIELD

Embodiments generally relate to fitness. More particularly, embodiments relate to wearable device normalization of fitness equipment settings and characteristics.

BACKGROUND

Treadmills may be common fitness equipment used by a wide variety of individuals in many different environments. For example, a particular individual may exercise on one treadmill located in a home gym and subsequently exercise on another treadmill located in a hotel gym (e.g., while traveling), wherein the two treadmills may have different manufacturers, options and/or settings. Thus, the differences between the two treadmills may prevent the individual from being able to determine whether the fitness/workout sessions on the two treadmills are equivalent. Moreover, different individuals may be unable to compete with one another during fitness sessions due to the differences between their respective treadmills.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1:
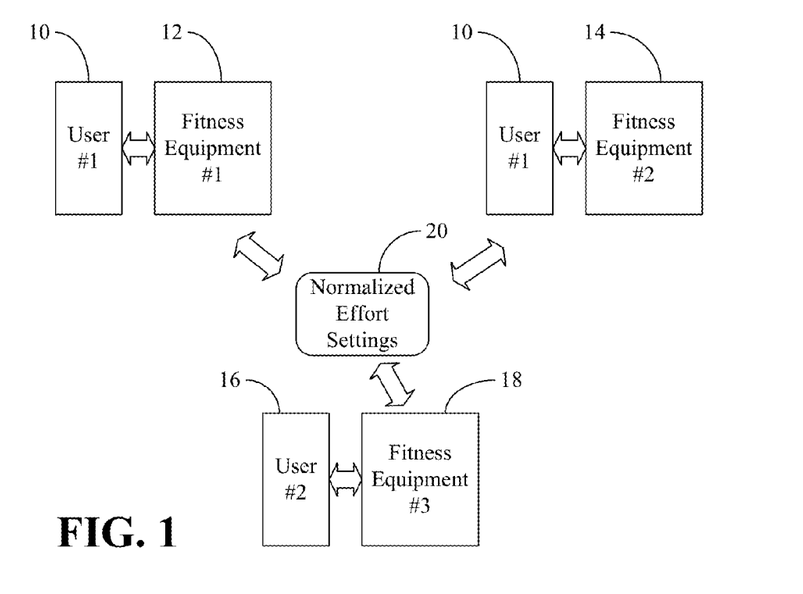
FIG. 1 is a block diagram of an example of an effort normalization according to an embodiment.

Turning now to FIG. 1, a fitness scenario is shown in which a first user 10 engages in a first fitness session (e.g., at time $t_0$) on first fitness equipment 12 such as, for example, a treadmill, elliptical trainer, weight machine, weight set, stationary bike, step machine, and so forth. The first fitness equipment 12 may generally have one or more settings that impact the amount of effort spent by the first user 10 during the first fitness session. For example, if the first fitness equipment 12 is a treadmill, the settings might include speed, incline, interval profile, etc. If, on the other hand, the first fitness equipment 12 is an elliptical trainer, the settings may include speed, resistance, interval profile, etc. The first user 10 may subsequently engage in a second fitness session (e.g., at time $t_1$) on second fitness equipment 14, wherein the second fitness equipment 14 may be the same type of equipment as the first fitness equipment 12 but originating from a different manufacturer or of a different model. For example, the first fitness equipment 12 may be a treadmill from Manufacturer #1 and the second fitness equipment 14 may be a treadmill from Manufacturer #2, the first fitness equipment 12 may be Model A of an elliptical trainer from Manufacturer #1 and the second fitness equipment 14 may be Model B of an elliptical trainer from Manufacturer #1, and so forth.

Accordingly, the second fitness equipment 14 may also have various settings that impact the amount of effort spent by the first user 10 during the second fitness session, wherein the settings of the second fitness equipment 14 differ from the settings of the first fitness equipment 12. For example, in the case of two different treadmills, the first fitness equipment 12 may have an incline setting that ranges from zero to ten and the second fitness equipment 14 may have an incline setting that ranges from zero to seven, wherein the degrees between each incline step may be different between the two treadmills. Similarly, in the case of two different elliptical trainers, the first fitness equipment 12 may have a resistance setting with a different range, minimum and/or maximum than the second fitness equipment 14.

Additionally, a second user 16 may engage in a third fitness session (e.g., at time $t_0$, $t_1$ or some other moment in time) on third fitness equipment 18, wherein the third fitness equipment 18 may be the same type of equipment as the first fitness equipment 12 and/or the second fitness equipment 14 but originating from a different manufacturer or of a different model. Accordingly, the third fitness equipment 18 may have one or more settings that differ from the settings of the second fitness equipment 14 and/or the settings of the first fitness equipment 12.

In the illustrated example, an effort normalization is conducted between the settings of the fitness equipment 12, 14, 18 in order to automatically generate normalized effort settings 20. The normalized effort settings 20 may enable the first user 10 to ensure that the amount of effort spent by the first user 10 during the second fitness session on the second fitness equipment 14 is equivalent to (or greater than) the amount of effort spent by the first user 10 during the first fitness session on the first fitness equipment 12. Moreover, the normalized effort settings 20 may enable the first user 10 and the second user 16 to compete with one another during the second fitness session on the second fitness equipment 14 and the third fitness session on the third fitness equipment, respectively. As will be discussed in greater detail, setting-specific user prompts may be generated to inform the users 10, 16 of the appropriate equipment settings to achieve the corresponding effort levels. Additionally, wearable sensor data may be used to conduct the effort normalization as well as generate the user prompts.

Figure 2A:
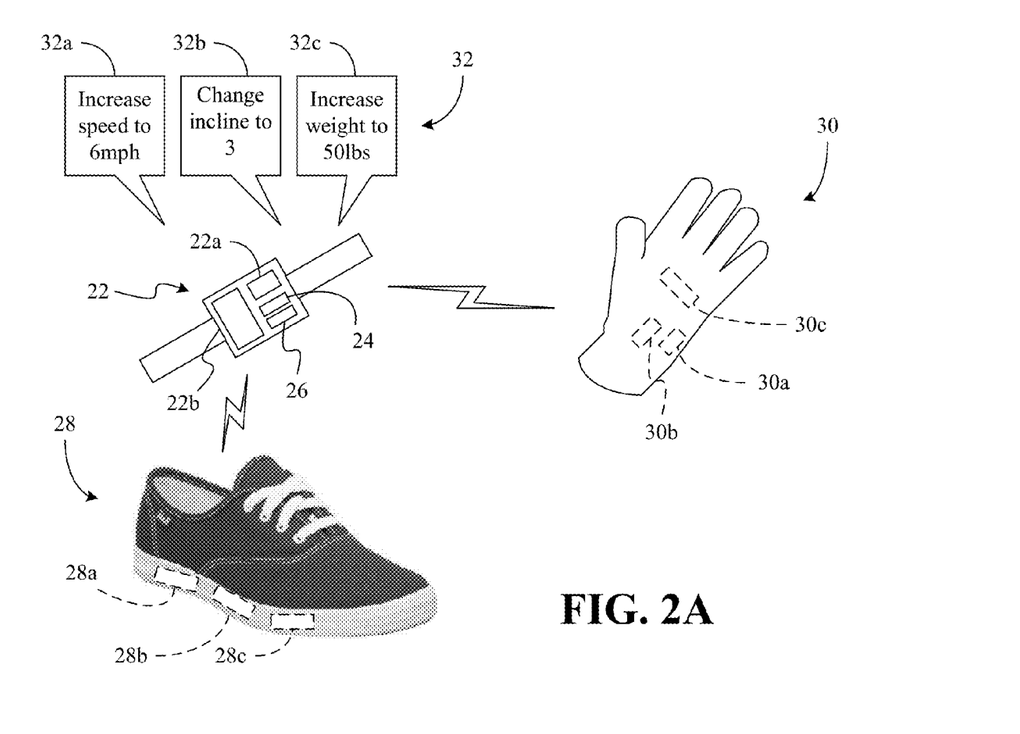
FIGS. 2A-2C are illustrations of examples of wearable sensor data configurations according to embodiments.

FIG. 2A shows a wearable sensor data configuration in which a first wearable device 22 (22a-22b) having a housing with a wearable form factor (e.g., watch form factor in the example shown). The illustrated first wearable device 22 includes logic 22a (e.g., implemented in logic instructions, configurable logic, fixed-functionality logic hardware, etc., or any combination thereof) to obtain first wearable sensor data 24 associated with a first fitness session and first fitness equipment such as, for example, the first fitness equipment 12 (FIG. 1). The first wearable sensor data 24 may be obtained from, for example, a second wearable device 28 (28a-28c, e.g., a smart shoe/footwear) worn by the user (e.g., on the foot) and/or a third wearable device 30 (30a-30c, e.g., a smart glove) worn by the user (e.g., on the hand) during the first fitness session. For example, the second wearable device 28 might include a battery 28a to provide power to the second wearable device 28, a motion sensor 28b (e.g., accelerometer, gyroscope) to measure the physical movement of the second wearable device 28, and a force sensor

28c (e.g., piezoelectric sensor) to measure forces applied by the wearer of the second wearable device 28 to the fitness equipment, and so forth.

Accordingly, the amount of movement (e.g., gait in the case of a treadmill) as well as the amount of pressure applied through the bottom of the second wearable device 28 (e.g., to a foot pedal in the case of a stationary bike) during the first fitness session may be measured and communicated wirelessly to the first wearable device 22 as the first wearable sensor data 24. The second wearable device 28 may also be used during a second fitness session (e.g., if worn by the same user) to obtain second wearable sensor data 26 associated with a second fitness session and second fitness equipment such as, for example, the second fitness equipment 14 (FIG. 1). The first wearable device 22 may include memory to store the first wearable sensor data 24 and the second wearable sensor data 26.

As already noted, the first wearable sensor data 24 may also be obtained from the third wearable device 30 worn by the user (e.g., on the hand) during the first fitness session. For example, the third wearable device 30 may include a battery 30a to provide power to the third wearable device 30, a motion sensor 30b (e.g., accelerometer, gyroscope) to measure the physical movement of the third wearable device 30b, and a force sensor 30c (e.g., piezoelectric sensor) to measure forces applied by the wearer of the third wearable device 30 to the fitness equipment, and so forth.

Accordingly, the amount of movement (e.g., repetition stroke length in the case of a weight machine) as well as the amount of pressure applied through the palm of the third wearable device 30 (e.g., to a handle grip in the case of an elliptical trainer) during the first fitness session may be measured and communicated wirelessly to the first wearable device 22 as the first wearable sensor data 24. The third wearable device 30 may also be used during the second fitness session (e.g., if worn by the same user) to obtain the second wearable sensor data 26 associated with the second fitness session and the second fitness equipment. In addition, wearable devices such as, for example, the wearable devices 22, 28, 30, may be worn by another user such as, for example, the second user 16 (FIG. 1) in order to obtain third wearable sensor data during a third fitness session. The first and second wearable sensor data 24, 26 may also include other types of data relevant to effort such as, for example, perspiration sensor data, temperature sensor data, heart rate sensor data, etc.

In the illustrated example, the logic 22a of the first wearable device 22 conducts an effort normalization between one or more settings of the first fitness equipment, the second fitness equipment and/or the third fitness equipment, and generates one or more user prompts 32 (32a-32c) during the second fitness session via a user interface 22b (UI, e.g., display, speaker, haptic/vibration component) based on the effort normalization. For example, the user prompts 32 might include a speed adjustment prompt 32a (e.g., "Increase speed to 6 mph"), an incline adjustment prompt 32b (e.g., "Change incline to 3"), a resistance adjustment prompt 32c (e.g., "Increase weight to 50 lbs"), etc., or any combination thereof, wherein compliance with the user prompts 32 may generally ensure that the individual asserts a target amount of effort.

Figure 2B:
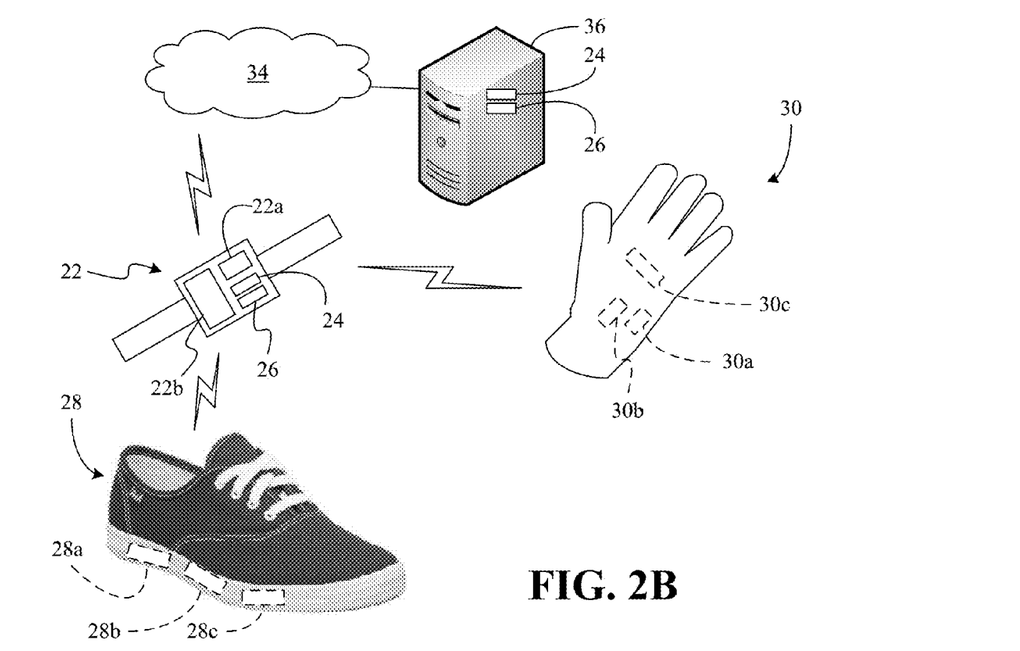
Figure 2C:
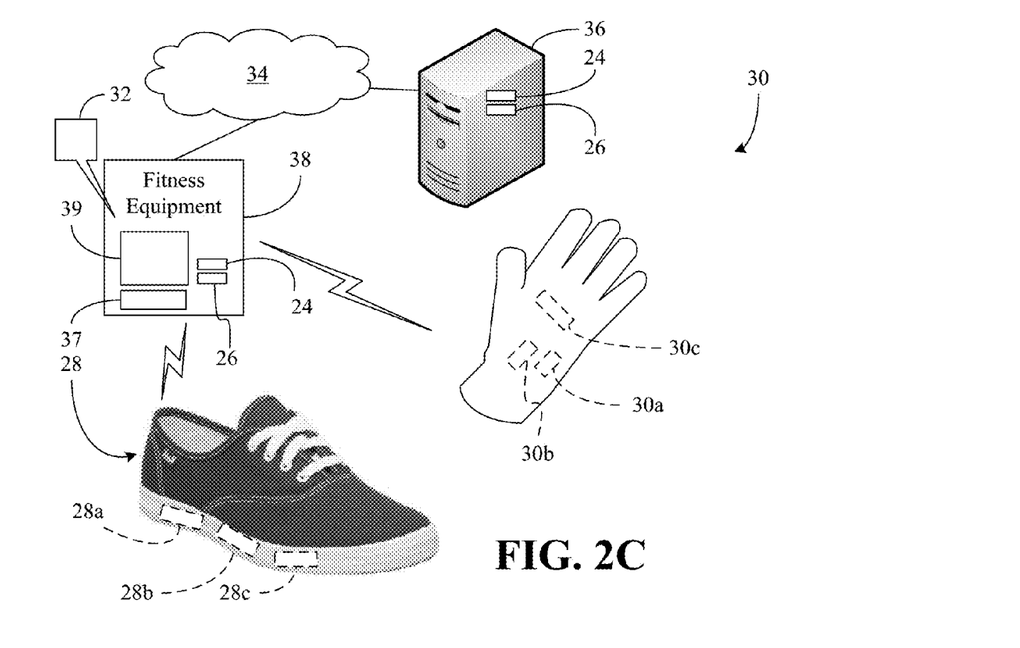

FIG. 2B demonstrates that the first wearable device 22 may also obtain the first wearable sensor data 24 and/or the second wearable sensor data 26 from a remote source such as a network 34 and/or a server 36. The illustrated solution may therefore be suitable in situations where, for example, the first and second wearable sensor data 24, 26 is associated with different users (e.g., who are competing with one another on their respective fitness equipment). The first wearable device 22 may also report locally obtained sensor data to the server 36. FIG. 2C demonstrates that fitness equipment 38 may include logic 37 to obtain the first and second wearable sensor data 24, 26, conduct the effort normalization and generate the user prompts 32 via a user interface 39 (e.g., display, speaker, haptic/vibration component).

Figure 3:
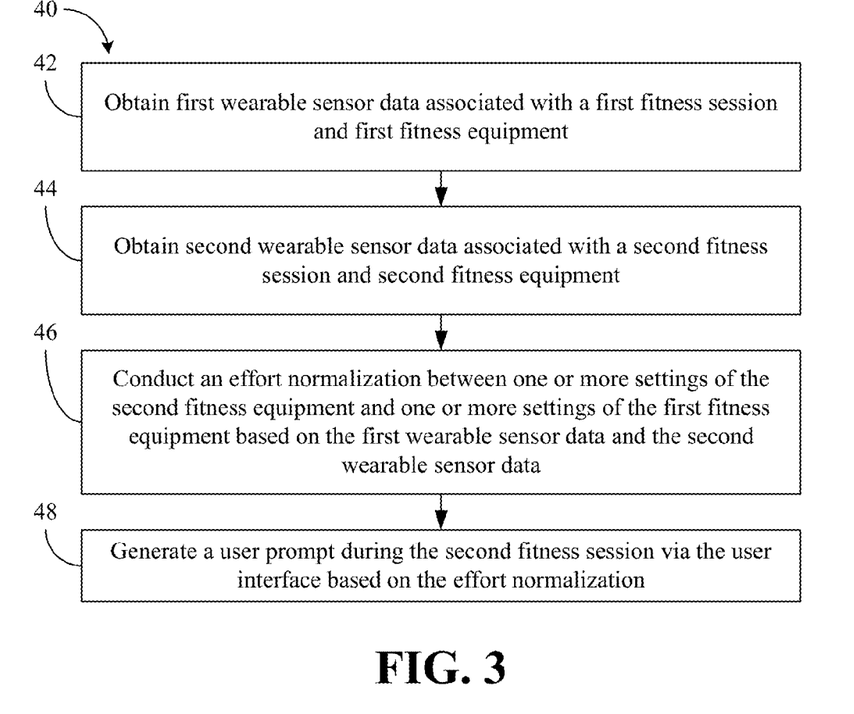
FIG. 3 is a flowchart of an example of a method of enhancing fitness sessions according to an embodiment.

FIG. 3 shows a method 40 of enhancing fitness sessions. The method 40 may generally be implemented in, for example, the first wearable device 22 (FIGS. 2A and 2B), the fitness equipment 12, 14 (FIG. 1), and/or the fitness equipment 38 (FIG. 2C), already discussed. More particularly, the method 40 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof.

Illustrated processing block 42 provides for obtaining first wearable sensor data associated with a first fitness session and first fitness equipment, wherein block 44 may obtain second wearable sensor data associated with a second fitness session and second fitness equipment. Additionally, illustrated block 46 conducts an effort normalization between one or more settings of the second fitness equipment and one or more settings of the first fitness equipment based on the first wearable sensor data and the second wearable sensor data. A user prompt may be generated at block 48 during the second fitness session via the user interface based on the effort normalization.

Figure 4:
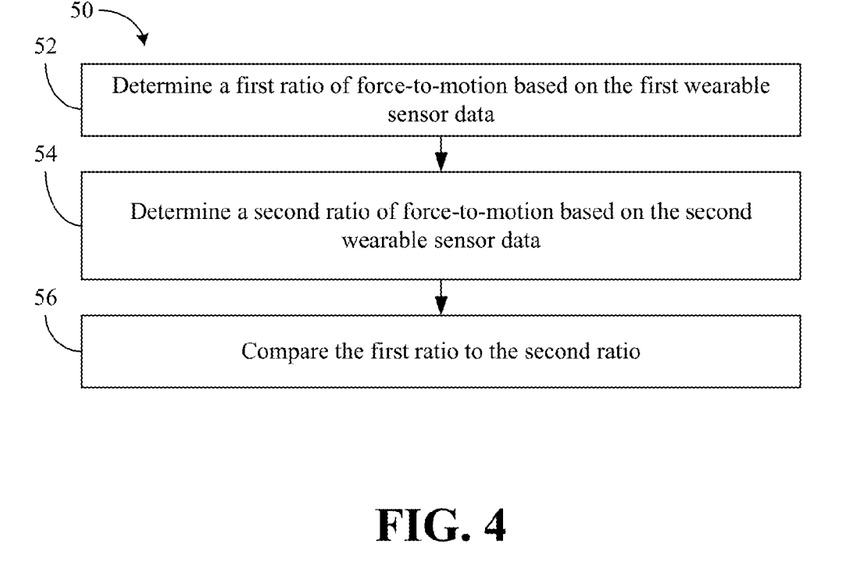
FIG. 4 is a block diagram of an example of a method of conducting effort normalizations according to an embodiment.

FIG. 4 shows a method 50 of conducting effort normalizations. The method 50, which may be readily incorporated into block 46 (FIG. 3), already discussed, may generally be implemented in, for example, the first wearable device 22 (FIGS. 2A and 2B), the fitness equipment 12, 14 (FIG. 1), and/or the fitness equipment 38 (FIG. 2C), already discussed. More particularly, the method 40 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated processing block 52 provides for determining a first ratio of force-to-motion based on first wearable sensor data. For example, block 52 might determine that the user is generating 1000 N of foot pressure at a stride length of 2.5 ft during a first fitness session on first fitness equipment. The first ratio may therefore be 400 N/ft in such a scenario. Block 54 may determine a second ratio of force-to-motion based on second wearable sensor data. For example, block 54 might determine that the user (e.g., either the same user or a different user) is generating 900 N of foot pressure at a stride length of 3.0 ft during a second fitness session on second fitness equipment. The second ratio may therefore be 300 N/ft in such a scenario. Illustrated block 56 provides for comparing the first ratio to the second ratio, wherein the first ratio and the second ratio represent a unit of effort.

Thus, in the above example, block 56 might determine that the user is asserting less effort in the second fitness session. In such as case, the user may be prompted to assert more effort by, for example, increasing speed, incline and/or resistance. Other approaches may also be used to conduct the effort normalization. For example, the ratio may contain one of multiple factors including perspiration sensor data, temperature sensor data, heart rate sensor data, microphone data, camera feeds, blood flow data, environmental data (e.g., ambient temperature, air pressure/barometer, altitude), time data (e.g., early morning versus late evening), location data (e.g., usual location versus hotel while traveling), etc., that may also be indicative of the level of effort being asserted by the user. Moreover, different ratios/measures may be created for different groups based on, for example, data from a single user.

In some embodiments of the method 50, the motion in the force-to-motion ratio may be a virtual unit of motion. For example, exercise equipment is often calibrated to give the user a mileage estimate that corresponds to cycles at a given force. In the case of an exercise equipment that acts as a stationary bicycle, a revolution of the pedal at a given force level may count as a "distance" unit, even though the equipment is stationary. In some cases, a number of units of credit may be given, wherein the credit correlates with duration or required force. In this case, the motion in the force-to-motion ratio may be such a unit that is not correlated to an estimated distance.

Figure 5:
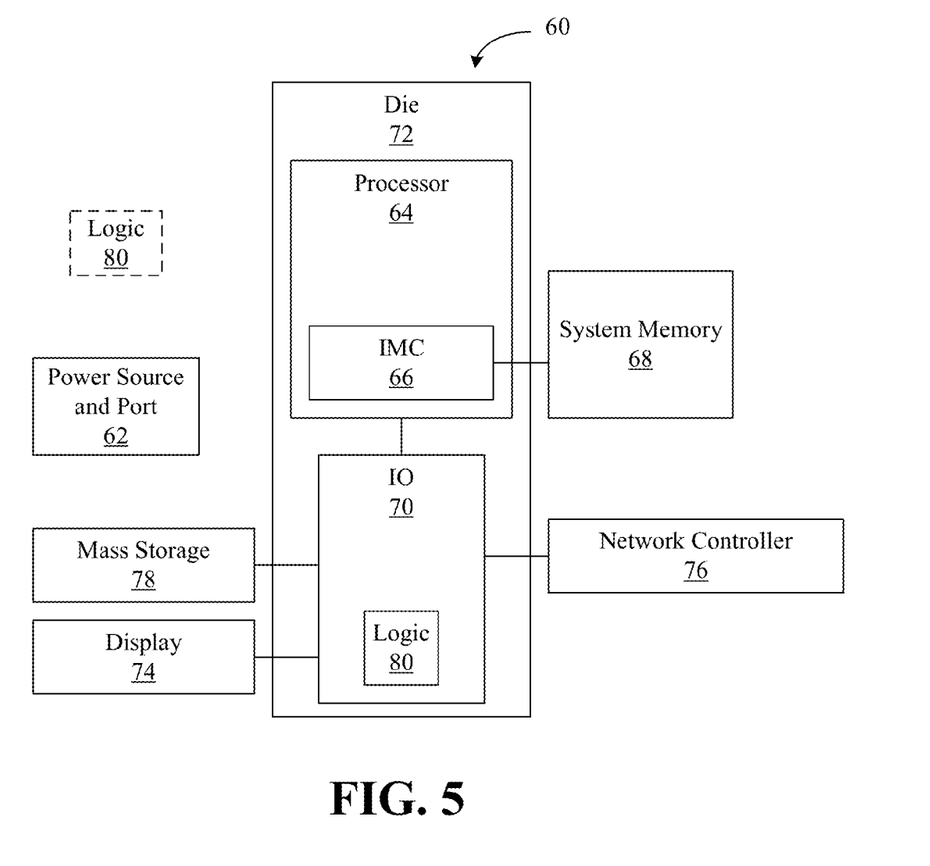
FIG. 5 is a block diagram of an example of a computing system according to an embodiment.

FIG. 6 shows a computing system 60. The computing system 60 may be part of an electronic device/platform having fitness functionality (e.g., treadmill, elliptical trainer, weight machine, weight set, stationary bike, step machine), computing functionality (e.g., personal digital assistant/PDA, notebook computer, tablet computer), communications functionality (e.g., smart phone), imaging functionality, media playing functionality (e.g., smart television/TV), wearable functionality (e.g., glove, watch, eyewear, headwear, footwear, jewelry), sensing functionality (e.g., Internet of Things/IoT device), etc., or any combination thereof. In the illustrated example, the system 60 includes a power source and port 62 to supply power to the system 60 and a processor 64 having an integrated memory controller (IMC) 66, which may communicate with system memory 68. The system memory 68 may include, for example, dynamic random access memory (DRAM) configured as one or more memory modules such as, for example, dual inline memory modules (DIMMs), small outline DIMMs (SODIMMs), etc.

The illustrated system 60 also includes an input output (IO) module 70 implemented together with the processor 64 on a semiconductor die 72 as a system on chip (SoC), wherein the IO module 70 functions as a host device and may communicate with, for example, a display 74 (e.g., touch screen, liquid crystal display/LCD, light emitting diode/LED display), a network controller 76 (e.g., Bluetooth radio, Wi-Fi radio), and mass storage 78 (e.g., hard disk drive/HDD, optical disk, flash memory, etc.). The illustrated IO module 70 may include logic 80 to obtain first wearable sensor data associated with a first fitness session and first fitness equipment, obtain second wearable data associated with a second fitness session and second fitness equipment, and conduct an effort normalization between one or more settings of the second fitness equipment and one or more settings of the first fitness equipment based on the first wearable sensor data and the second wearable sensor data. Thus, the logic 80 may have functionality similar to that of the logic 22a (FIGS. 2A and 2B) and/or the logic 37 (FIG. 2C). Additionally, the logic 80 may implement one or more aspects of the method 40 (FIG. 3) and/or the method 50 (FIG. 4). The logic 80 may also be implemented elsewhere in the system 60. Accordingly, the semiconductor die 72 may function as a fitness session enhancement apparatus.

Additional Notes and Examples

Example 1 may include a wearable device comprising a housing having a wearable form factor, a battery port to receive power for the device, and logic to obtain first wearable sensor data associated with a first fitness session and first fitness equipment, obtain second wearable sensor data associated with a second fitness session and second fitness equipment, and conduct an effort normalization between one or more settings of the second fitness equipment and one or more settings of the first fitness equipment based on the first wearable sensor data and the second wearable sensor data.

Example 2 may include the device of Example 1, further including a user interface, wherein the logic is to generate a user prompt during the second fitness session via the user interface based on the effort normalization.

Example 3 may include the device of Example 2, wherein the user prompt is to include one or more of a speed adjustment prompt, an incline adjustment prompt or a resistance adjustment prompt.

Example 4 may include the device of Example 1, wherein the logic is to determine a first ratio of force-to-motion based on the first wearable sensor data, determine a second ratio of force-to-motion based on the second wearable sensor data, and compare the first ratio to the second ratio to conduct the effort normalization, wherein the first ratio and the second ratio are to represent a unit of effort.

Example 5 may include the device of any one of Examples 1 to 4, wherein the first wearable sensor data and the second wearable sensor data are to be obtained from one or more of footwear or a glove and the first wearable sensor data and the second wearable sensor data are to include one or more of pressure sensor data, motion sensor data, perspiration sensor data, temperature sensor data or heart rate sensor data.

Example 6 may include the device of any one of Examples 1 to 4, wherein the first wearable sensor data and the second wearable sensor data are to be associated with one or more of different treadmills, different elliptical trainers, different weight machines, different weight sets, different stationary bikes, or different step machines.

Example 7 may include a fitness session enhancement apparatus comprising logic, implemented at least partly in one or more of configurable logic or fixed-functionality logic hardware, to obtain first wearable sensor data associated with a first fitness session and first fitness equipment, obtain second wearable sensor data associated with a second fitness session and second fitness equipment, and conduct an effort normalization between one or more settings of the second fitness equipment and one or more settings of the first fitness equipment based on the first wearable sensor data and the second wearable sensor data.

Example 8 may include the apparatus of Example 7, wherein the logic is to generate a user prompt during the second fitness session via a user interface of one or more of the second fitness equipment or a wearable device based on the effort normalization.

Example 9 may include the apparatus of Example 8, wherein the user prompt is to include one or more of a speed adjustment prompt, an incline adjustment prompt or a resistance adjustment prompt.

Example 10 may include the apparatus of Example 7, wherein the logic is to determine a first ratio of force-to-motion based on the first wearable sensor data, determine a second ratio of force-to-motion based on the second wearable sensor data, and compare the first ratio to the second ratio to conduct the effort normalization, wherein the first ratio and the second ratio are to represent a unit of effort.

Example 11 may include the apparatus of any one of Examples 7 to 10, wherein the first wearable sensor data and the second wearable sensor data are to be obtained from one or more of footwear or a glove and the first wearable sensor data and the second wearable sensor data are to include one or more of pressure sensor data, motion sensor data, perspiration sensor data, temperature sensor data or heart rate sensor data.

Example 12 may include the apparatus of any one of Examples 7 to 10, wherein the first wearable sensor data and the second wearable sensor data are to be associated with one or more of different treadmills, different elliptical trainers, different weight machines, different weight sets, different stationary bikes, or different step machines.

Example 13 may include a method of operating a fitness session enhancement apparatus, comprising obtaining first wearable sensor data associated with a first fitness session and first fitness equipment, obtaining second wearable sensor data associated with a second fitness session and second fitness equipment, and conducting an effort normalization between one or more settings of the second fitness equipment and one or more settings of the first fitness equipment based on the first wearable sensor data and the second wearable sensor data.

Example 14 may include the method of Example 13, further including generating a user prompt during the second fitness session via a user interface of one or more of the second fitness equipment or a wearable device based on the effort normalization.

Example 15 may include the method of Example 14, wherein the user prompt includes one or more of a speed adjustment prompt, an incline adjustment prompt or a resistance adjustment prompt.

Example 16 may include the method of Example 13, wherein conducting the effort normalization includes determining a first ratio of force-to-motion based on the first wearable sensor data, determining a second ratio of force-to-motion based on the second wearable sensor data, and comparing the first ratio to the second ratio, wherein the first ratio and the second ratio represent a unit of effort.

Example 17 may include the method of any one of Examples 13 to 16, wherein the first wearable sensor data and the second wearable sensor data are obtained from one or more of footwear or a glove and the first wearable sensor data and the second wearable sensor data includes one or more of pressure sensor data, motion sensor data, perspiration sensor data, temperature sensor data or heart rate sensor data.

Example 18 may include the method of any one of Examples 13 to 16, wherein the first wearable sensor data and the second wearable sensor data are associated with one or more of different treadmills, different elliptical trainers, different weight machines, different weight sets, different stationary bikes, or different step machines.

Example 19 may include at least one non-transitory computer readable storage medium comprising a set of instructions, which when executed by a computing device, cause the computing device to obtain first wearable sensor data associated with a first fitness session and first fitness equipment, obtain second wearable sensor data associated with a second fitness session and second fitness equipment, and conduct an effort normalization between one or more settings of the second fitness equipment and one or more settings of the first fitness equipment based on the first wearable sensor data and the second wearable sensor data.

Example 20 may include the at least one non-transitory computer readable storage medium of Example 19, wherein the instructions, when executed, cause a computing device to generate a user prompt during the second fitness session via a user interface of one or more of the second fitness equipment or a wearable device based on the effort normalization.

Example 21 may include the at least one non-transitory computer readable storage medium of Example 20, wherein the user prompt is to include one or more of a speed adjustment prompt, an incline adjustment prompt or a resistance adjustment prompt.

Example 22 may include the at least one non-transitory computer readable storage medium of Example 19, wherein the instructions, when executed, cause a computing device to determine a first ratio of force-to-motion based on the first wearable sensor data, determine a second ratio of force-to-motion based on the second wearable sensor data, and compare the first ratio to the second ratio to conduct the effort normalization, wherein the first ratio and the second ratio are to represent a unit of effort.

Example 23 may include the at least one non-transitory computer readable storage medium of any one of Examples 19 to 22, wherein the first wearable sensor data and the second wearable sensor data are to be obtained from one or more of footwear or a glove and the first wearable sensor data and the second wearable sensor data are to include one or more of pressure sensor data, motion sensor data, perspiration sensor data, temperature sensor data or heart rate sensor data.

Example 24 may include the at least one non-transitory computer readable storage medium of any one of Examples 19 to 22, wherein the first wearable sensor data and the second wearable sensor data are to be associated with one or more of different treadmills, different elliptical trainers, different weight machines, different weight sets, different stationary bikes, or different step machines.

Example 25 may include the at least one non-transitory computer readable storage medium of any one of Examples 19 to 22, wherein the first wearable sensor data and the second wearable sensor data are to be associated with different users.

Example 26 may include a fitness session enhancement apparatus comprising means for obtaining first wearable sensor data associated with a first fitness session and first fitness equipment, means for obtaining second wearable sensor data associated with a second fitness session and second fitness equipment, and means for conducting an effort normalization between one or more settings of the second fitness equipment and one or more settings of the first fitness equipment based on the first wearable sensor data and the second wearable sensor data.

Example 27 may include the apparatus of Example 26, further means for including generating a user prompt during the second fitness session via a user interface of one or more of the second fitness equipment or a wearable device based on the effort normalization.

Example 28 may include the apparatus of Example 27, wherein the user prompt is to include one or more of a speed adjustment prompt, an incline adjustment prompt or a resistance adjustment prompt.

Example 29 may include the apparatus of Example 26, wherein the means for conducting the effort normalization includes means for determining a first ratio of force-to-motion based on the first wearable sensor data, means for determining a second ratio of force-to-motion based on the second wearable sensor data, and means for comparing the first ratio to the second ratio.

Example 30 may include the apparatus of any one of Examples 26 to 29, wherein the first wearable sensor data and the second wearable sensor data are to be obtained from one or more of footwear or a glove and the first wearable sensor data and the second wearable sensor data is to include one or more of pressure sensor data, motion sensor data, perspiration sensor data, temperature sensor data or heart rate sensor data.

Example 31 may include the apparatus of any one of Examples 26 to 29, wherein the first wearable sensor data and the second wearable sensor data are to be associated with one or more of different treadmills, different elliptical trainers, different weight machines, different weight sets, different stationary bikes, or different step machines.

Techniques described herein may therefore address concerns over workout difficulty by gathering workout characteristics (e.g., using a low pass filter) of recorded sensor data to determine static inclination, speed and other configurable settings on the fitness equipment. Such an approach may ensure that the workout selection by a first user may be "replayed" for competitors. Although sensor data may only be shared within specified groups, the system may also use the data (e.g., as part of an opt-in agreement) to suggest other public groups/competitions in which the user may want to participate (e.g., to maintain or increase workout difficulty). The system may also take advantage of a single individual who uses multiple equipment instances. Such an approach may enable equipment comparisons to be calibrated from the same set of sensors and the same individual wearing those sensors. Measures from this individual might be weighted with other data gathered from individuals who do not use both sets of equipment (e.g., enabling that individual's data to improve the comparisons being made for other individuals).

Additionally, comparative "effort" may be determined on the basis of HR (heart rate), perspiration, weight, and environmental factors (e.g., humidity, temperature), and so forth. Simply put, techniques may provide for a "unit of effort" that explicitly measures comparative effort. Such an approach may be useful for individuals who maintain effort across a training regime—over time the individual becomes fitter and what was once an effortful workout may become easier. The unit of effort may therefore enable the user to maintain effort across changing levels of fitness.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A device comprising:
   a housing having a wearable form factor;
   a battery port to receive power for the device; and
   a processor programmed to:
      obtain, from one or more sensors, first wearable sensor data associated with a first fitness session and first fitness equipment,
      obtain, from the one or more sensors, second wearable sensor data associated with a second fitness session and second fitness equipment,
      determine a first ratio of force-to-motion based on the first wearable sensor data,
      determine a second ratio of force-to-motion based on the second wearable sensor data,
      compare the first ratio of force-to-motion to the second ratio of force-to-motion to conduct an effort normalization, and
      conduct the effort normalization between one or more settings of the second fitness equipment and one or more settings of the first fitness equipment based on the first wearable sensor data and the second wearable sensor data.

2. The device of claim 1, further including a user interface, wherein the processor generates a user prompt during the second fitness session via the user interface based on the effort normalization.

3. The device of claim 2, wherein the user prompt includes one or more of a speed adjustment prompt, an incline adjustment prompt or a resistance adjustment prompt.

4. The device of claim 1, wherein the first ratio of force-to-motion and the second ratio of force-to-motion represent a unit of effort.

5. The device of claim 1, wherein the first wearable sensor data and the second wearable sensor data are to be obtained from one or more of footwear or a glove and the first wearable sensor data and the second wearable sensor data are to include one or more of pressure sensor data, motion sensor data, perspiration sensor data, temperature sensor data or heart rate sensor data.

6. The device of claim 1, wherein the first wearable sensor data and the second wearable sensor data are to be associated with one or more of different treadmills, different elliptical trainers, different weight machines, different weight sets, different stationary bikes, or different step machines.

* * * * *